(12) United States Patent
Rosemberg et al.

(10) Patent No.: US 8,603,015 B2
(45) Date of Patent: Dec. 10, 2013

(54) METHOD AND SYSTEM FOR MONITORING ABLATION OF TISSUES

(75) Inventors: Yossef Rosemberg, RaAnana (IL); Arie Orenstein, Tel-Aviv (IL)

(73) Assignee: Tel Hashomer Medical Research Infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 13/267,232

(22) Filed: Oct. 6, 2011

(65) Prior Publication Data

US 2012/0029497 A1    Feb. 2, 2012

Related U.S. Application Data

(60) Continuation of application No. 12/068,621, filed on Feb. 8, 2008, now abandoned, which is a division of application No. 11/008,979, filed on Dec. 13, 2004, now Pat. No. 7,367,944.

(51) Int. Cl.
*A61H 1/00* (2006.01)

(52) U.S. Cl.
USPC ........ 601/3; 601/2; 601/4; 600/407; 600/437; 600/439; 600/443; 600/447

(58) Field of Classification Search
USPC ........... 600/407, 437, 439, 443, 447; 601/2–4
See application file for complete search history.

(56) References Cited

U.S. PATENT DOCUMENTS

| | | | |
|---|---|---|---|
| 4,183,011 A | 1/1980 | Massa | |
| 4,211,489 A | 7/1980 | Kleinknecht et al. | |
| 4,271,490 A | 6/1981 | Minohara et al. | |
| 4,297,607 A | 10/1981 | Lynnworth et al. | |
| 4,433,399 A | 2/1984 | Massa | |
| 4,452,081 A | 6/1984 | Seppi | |
| 4,501,186 A | 2/1985 | Ikuma | |
| 4,554,834 A | 11/1985 | Prinz et al. | |
| 4,576,047 A | 3/1986 | Lauer et al. | |
| 4,577,506 A | 3/1986 | Poole et al. | |
| 4,630,072 A | 12/1986 | Scardovi et al. | |
| 4,641,291 A | 2/1987 | Simmons, Sr. et al. | |
| 4,672,592 A | 6/1987 | Skinner | |
| 4,814,552 A | 3/1989 | Stefik et al. | |
| 4,924,466 A | 5/1990 | Gregor et al. | |
| 4,991,148 A | 2/1991 | Gilchrist | |
| 5,062,089 A | 10/1991 | Willard et al. | |
| 5,138,159 A | 8/1992 | Takase et al. | |
| 5,142,506 A | 8/1992 | Edwards | |
| 5,163,094 A * | 11/1992 | Prokoski et al. | ............... 382/118 |
| 5,245,863 A | 9/1993 | Kajimura et al. | |
| 5,372,138 A | 12/1994 | Crawley et al. | |

(Continued)

FOREIGN PATENT DOCUMENTS

| EP | 0312481 | 4/1989 |
|---|---|---|
| EP | 0666543 | 8/1995 |

(Continued)

*Primary Examiner* — Joel Lamprecht
(74) *Attorney, Agent, or Firm* — The Law Office of Joseph L. Felber

(57) ABSTRACT

A method of monitoring heat damage to a tissue during a heat ablation procedure is disclosed. The method comprising: providing images of the tissue, extracting at least one parameter being indicative of a biological response to heat, and using the parameter(s) for determining the heat damage to the tissue.

39 Claims, 8 Drawing Sheets

(56) References Cited

U.S. PATENT DOCUMENTS

| | | |
|---|---|---|
| 5,391,197 A | 2/1995 | Burdette et al. |
| 5,394,741 A | 3/1995 | Kajimura et al. |
| 5,421,338 A | 6/1995 | Crowley et al. |
| 5,432,346 A | 7/1995 | Nose et al. |
| 5,433,717 A | 7/1995 | Rubinsky et al. |
| 5,511,043 A | 4/1996 | Lindberg |
| 5,515,853 A | 5/1996 | Smith et al. |
| 5,517,579 A | 5/1996 | Baron et al. |
| 5,519,686 A | 5/1996 | Yanagisawa et al. |
| 5,524,630 A | 6/1996 | Crowley |
| 5,530,683 A | 6/1996 | Lindberg |
| 5,550,791 A | 8/1996 | Peloquin et al. |
| 5,588,432 A | 12/1996 | Crowley |
| 5,657,760 A | 8/1997 | Ying et al. |
| 5,682,445 A | 10/1997 | Smith |
| 5,702,629 A | 12/1997 | Cui et al. |
| 5,715,825 A | 2/1998 | Crowley |
| 5,720,720 A | 2/1998 | Laske et al. |
| 5,721,721 A | 2/1998 | Yanagisava et al. |
| 5,794,175 A | 8/1998 | Conner |
| 5,840,031 A | 11/1998 | Crowley |
| 5,866,856 A | 2/1999 | Holtzman |
| 5,895,356 A | 4/1999 | Andrus et al. |
| 5,941,832 A * | 8/1999 | Tumey et al. .................. 600/549 |
| 5,977,958 A | 11/1999 | Baron et al. |
| 6,004,269 A | 12/1999 | Crowley et al. |
| 6,026,316 A | 2/2000 | Kucharczyk et al. |
| 6,050,943 A | 4/2000 | Slayton et al. |
| 6,111,565 A | 8/2000 | Chery et al. |
| 6,137,621 A | 10/2000 | Wu |
| 6,147,681 A | 11/2000 | Chery et al. |
| 6,151,014 A | 11/2000 | Zloter et al. |
| 6,169,281 B1 | 1/2001 | Chen et al. |
| 6,211,863 B1 | 4/2001 | Chery et al. |
| 6,232,962 B1 | 5/2001 | Davis et al. |
| 6,252,656 B1 | 6/2001 | Wu et al. |
| 6,265,676 B1 | 7/2001 | Zloter et al. |
| 6,282,340 B1 | 8/2001 | Nasu et al. |
| 6,292,177 B1 | 9/2001 | Holtzman et al. |
| 6,292,180 B1 | 9/2001 | Lee |
| 6,298,259 B1 | 10/2001 | Kucharczyk et al. |
| 6,300,580 B1 | 10/2001 | Shenholtz et al. |
| 6,367,335 B1 | 4/2002 | Hicks |
| 6,392,230 B1 | 5/2002 | Aita |
| 6,392,330 B1 | 5/2002 | Zloter et al. |
| 6,424,340 B1 | 7/2002 | Holtzman et al. |
| 6,430,342 B1 | 8/2002 | Kim et al. |
| 6,451,015 B1 | 9/2002 | Rittman, III et al. |
| 6,485,413 B1 | 11/2002 | Boppart et al. |
| 6,500,121 B1 | 12/2002 | Slayton et al. |
| 6,504,289 B2 | 1/2003 | Toda et al. |
| 6,508,774 B1 | 1/2003 | Acker et al. |
| 6,577,299 B1 | 6/2003 | Schiller et al. |
| 6,681,635 B1 | 1/2004 | Van Schaik |
| 6,716,184 B2 | 4/2004 | Vaezy et al. |
| 6,724,371 B1 | 4/2004 | Shenholtz et al. |
| 6,738,408 B2 | 5/2004 | Abedin |
| 6,745,632 B1 | 6/2004 | Dryer et al. |
| 6,771,006 B2 | 8/2004 | Zloter et al. |
| 6,778,735 B2 | 8/2004 | Miller et al. |
| 6,816,266 B2 | 11/2004 | Varshneya et al. |
| 6,822,641 B2 | 11/2004 | Shenholtz et al. |
| 6,823,105 B2 | 11/2004 | Zloter et al. |
| 6,831,781 B2 | 12/2004 | Tearney et al. |
| 6,832,342 B2 | 12/2004 | Fields et al. |
| 6,841,742 B2 | 1/2005 | Shenholtz et al. |
| 6,873,415 B2 | 3/2005 | Amonette et al. |
| 7,211,044 B2 * | 5/2007 | Mast et al ..................... 600/439 |
| 7,367,944 B2 | 5/2008 | Rosemberg et al. |
| 2002/0031243 A1 | 3/2002 | Schiller et al. |
| 2002/0052311 A1 | 5/2002 | Solomon et al. |
| 2003/0095708 A1 | 5/2003 | Pittel |
| 2003/0142065 A1 | 7/2003 | Pahlavan |
| 2004/0032399 A1 | 2/2004 | Sekiguchi et al. |
| 2004/0106870 A1 | 6/2004 | Mast |
| 2004/0267120 A1 | 12/2004 | Podany et al. |
| 2005/0150697 A1 | 7/2005 | Altman et al. |

FOREIGN PATENT DOCUMENTS

| | | |
|---|---|---|
| EP | 1450296 | 8/2004 |
| EP | 1504330 | 8/2006 |
| GB | 2043899 | 10/1980 |
| GB | 2121174 | 12/1983 |
| TW | 394833 | 6/2000 |
| WO | WO 0021203 | 4/2000 |
| WO | WO 0135329 | 5/2001 |
| WO | WO 03069547 | 1/2002 |
| WO | WO 03069547 | 8/2003 |
| WO | WO 03088136 | 10/2003 |
| WO | WO 2004010592 | 1/2004 |
| WO | WO 2006031348 | 4/2005 |
| WO | WO 2005111653 | 11/2005 |
| WO | WO 2006035443 | 4/2006 |
| WO | WO 2006035444 | 4/2006 |
| WO | WO 2006064495 | 6/2006 |
| WO | WO 2006100682 | 9/2006 |

* cited by examiner

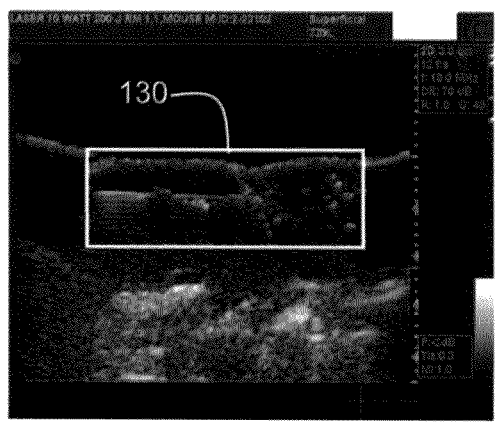 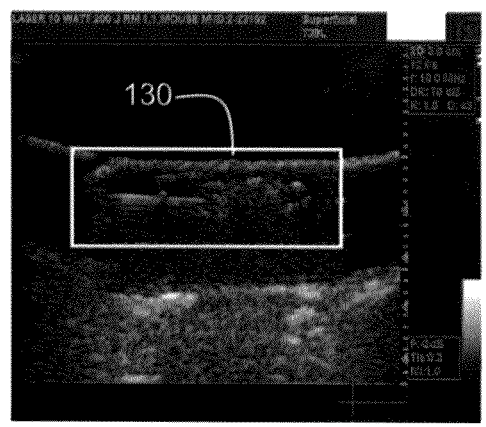
Fig. 6a                    Fig. 6b
 
Fig. 7a                    Fig. 7b
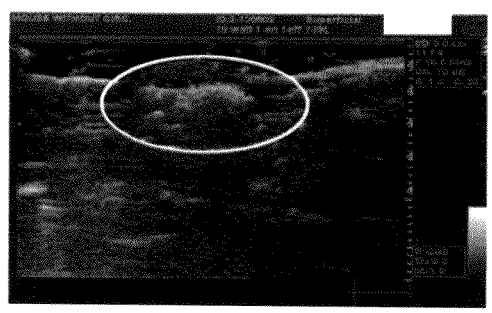 
Fig. 7c                    Fig. 7d

METHOD AND SYSTEM FOR MONITORING ABLATION OF TISSUES

RELATED APPLICATIONS

This Application is a Divisional of U.S. patent application Ser. No. 11/008,979, filed on Dec. 13, 2004.

FIELD AND BACKGROUND OF THE INVENTION

The present invention relates to the monitoring of tissue ablation, and more particularly, to a method and system for monitoring ablation of tissue by determining a biological response of the tissue to heat.

Cancer is a major cause of death in the modern world. Effective treatment of cancer is most readily accomplished following early detection of malignant tumors. Most techniques used to treat cancer (other than chemotherapy) are directed against a defined tumor site in an organ, such as brain, breast, ovary and colon, etc. Removal of a consolidated mass of abnormal cells is possible by surgical excision, heating, cooling, irradiative or chemical ablation.

Minimal invasive thermal therapy is a potential treatment for solid internal malignancies. This type of therapy provides for shorter hospital stays, faster recovery and better cosmetic results. In thermal therapy, heat is produced by devices inserted directly into a target site within an organ. Potentially less invasive than conventional surgery, this approach enables the treatment of tumors in otherwise inaccessible locations. Several devices have been employed for interstitial heating, including laser irradiation devices, radiofrequency ablation devices, high-focus ultrasound devices, microwave devices and the like. These devices have been shown to be capable of generating temperature elevations sufficient for thermal coagulation of tissue.

For example, radiofrequency ablation destroys tumor tissue by heat through laparoscopic application of mild, almost painless high-frequency energy applied directly to the tumor. More specifically, when an alternating electric field is created within the tissue, ions are agitated in the region neighboring the electric field source (typically an electrode). This ionic agitation creates friction and induces thermal injury to the tissue.

Radiofrequency ablation, however, is mainly applied to hepatic tumors, or tumors that are not close to a major blood vessel, due to its insufficient accuracy. The fact that the liver is a large enough organs could permit enough safety margins.

Destruction of unwanted cells via laser light can be achieved either through a direct thermal interaction between the laser beam and the tissue, or through activation of some photochemical reactions using light-activated molecules which are injected into or otherwise administered to the tissue.

The use of ultrasound for healing purposes has increased in importance. Depending on the therapy, ultrasound is applied in the form of continuous or pulsed ultrasound wave fields. The desire to generate rapid, localized temperature increases in tissue has led to the development of focused ultrasound as a method to treat tumors. In high-focus ultrasound treatment an ultrasound transducer generates focused ultrasound waves which are transmitted to the tumor. By special control of the time the focused ultrasound waves act on the tumor, resulting in an overheating of the tissue hence leading to its destruction. High-focus ultrasound can be employed by external or interstitial ultrasound transducers. To date, interstitial transducers have been developed for a variety of applications including cardiac ablation, prostate cancer ablation and gastrointestinal coagulation.

Several characteristics of the above prior art thermal therapy devices, however, limit their ability to treat large volumes or regions close to important anatomical structures. High temperatures close to the device surface often leads to undesirable physical effects of charring or vaporization in tissue. Inadequate heating can occur at the target boundary due to rapid decreases in deposited power with increasing distance from the device. Generally, the goal with interstitial thermal devices is to deliver a target-specific heating pattern which is as uniform as possible to the entire target volume of tissue, while avoiding excessive or inadequate heating.

Irrespectively of the method which is used to ablate the tumor, it is recognized that success of the treatment depends on the ability to monitor the ablation process [Hyunchul Rhim, et al., Radiographics, 2001, 21:S17-S35]. Thus, the use of minimal invasive thermal therapy is limited by the ability to monitor, hence control the destruction process precisely while it is being administered. Such precise control is required in order to minimize injury to normal adjacent parenchyma while assuring complete destruction of the offending lesion. The transfer of heat energy to the target depends on the efficiency with which the tissue absorbs the applied energy, and is therefore a function of tissue composition. Heat conduction through diffusion and perfusion processes may vary locally as a function of tissue architecture, tissue composition, local physiological parameters and the temperature itself. During ablation procedures, heat transfer characteristics may change as tissue coagulation can significantly modify heat conduction and energy absorption.

Several approaches are known in the art for monitoring the response of the treated tissue during treatment. For example, in radiofrequency ablation, commercially available devices include a thermal monitoring circuit which is integrated in the radiofrequency probe.

In another approach, impedance and capacitance-related parameters are measured and tracked during the ablation procedure to estimate tissue temperature. These techniques, however, only measure the temperature at isolated locations and cannot show the temperature distribution in the volume surrounding the destructing device. Efficient and accurate monitoring can be achieved by MRI, which can provide a reliable temperature mapping of the tissue. However, this MRI is an expensive procedure which imposes serious constrains to the surgical scenario.

In laser ablation, particularly in the area of skin disorders or in fully invasive procedures, the ablative procedure can be monitored optically using an optical fiber and a CCD camera coupled to a video monitor. A major disadvantage of this method is that it is limited to surfaces and the difficulty to apply this technique in minimal invasive procedure without significantly modifying the procedure's scenario.

An additional technique to monitor ablative procedure includes the use of ultrasound imaging. Attempts to adapt ultrasound imaging for temperature measurements include measurements of various ultrasound parameters such as the speed of sound, frequency shifts and the like. These approaches, however, have failed to provide the information required for minimizing injury to normal tissue while ablating the tumor.

There is thus a widely recognized need for a diagnostic ultrasound based monitoring method, and it would be highly advantageous to have such a method and system for monitoring ablation of tissue, devoid of the above limitations.

SUMMARY OF THE INVENTION

It is the object of the present invention to provide a method and system for monitoring the ablation of a tissue. Said monitoring is based on the understanding of the biological processes that the ablated tissue and/or its neighboring tissue undergo during the ablation process. Specifically, according to various exemplary embodiments of the present invention damage to the tissue is determined by analyzing images of the region-of-interest such as to extract the biological response to heat generated during the ablation procedure.

Thus, according to one aspect of the present invention there is provided a method of monitoring heat damage to a tissue during a heat ablation procedure. The method comprises providing images of the tissue, extracting at least one parameter being indicative of a biological response to heat, and using the at least one parameter for determining the heat damage to the tissue.

According to further features in preferred embodiments of the invention described below, the images are selected from the group consisting of ultrasound images, magnetic resonance images, X-ray images and gamma images.

According to still further features in the described preferred embodiments the tissue is a neighboring tissue to a tissue being heat ablated during the heat ablation procedure.

According to still further features in the described preferred embodiments the tissue is a tissue being heat ablated during the heat ablation procedure.

According to another aspect of the present invention there is provided a method of destructing a target tissue. The method comprises: delivering energy at a predetermined rate so as to heat the target tissue; providing images of at least a neighboring tissue to the target tissue; extracting at least one parameter being indicative of a biological response to heat; using the at least one parameter for determining a damage to the neighboring tissue; and if the neighboring tissue is damaged then ceasing the delivery of the energy.

According to further features in preferred embodiments of the invention described below, the target tissue forms a part of an organ.

According to still further features in the described preferred embodiments the target tissue forms a part of a tumor.

According to still further features in the described preferred embodiments the target tissue forms a part of a malignant tumor.

According to still further features in the described preferred embodiments the target tissue forms a part of a pathological tissue.

According to still further features in the described preferred embodiments the energy is delivered in a form of an alternating electric field.

According to still further features in the described preferred embodiments the energy is delivered in a form of a laser light.

According to still further features in the described preferred embodiments the energy is delivered in a form of a focused ultrasound.

According to still further features in the described preferred embodiments the energy is delivered in a form of a microwave.

According to still further features in the described preferred embodiments the biological response comprises heat convection via body liquid flow or lack thereof.

According to still further features in the described preferred embodiments the biological response comprises changes in blood circulation viability.

According to still further features in the described preferred embodiments the determination of the damage to the tissue comprises defining a damage-onset when the changes in the blood circulation viability are above a predetermined threshold.

According to still further features in the described preferred embodiments the biological response comprises accumulation of bubbles near the tissue, while the heating is at a substantial constant rate.

According to still further features in the described preferred embodiments the determination of the damage to the tissue comprises defining a damage-onset when the accumulation of the bubbles near the tissue is above a predetermined threshold.

According to still further features in the described preferred embodiments the biological response comprises disappearance of bubbles along a non-random pattern, while the heating is at a substantial constant rate.

According to still further features in the described preferred embodiments the method further comprises determining that the tissue is viable if the disappearance of the bubbles along the non-random pattern occurs.

According to still further features in the described preferred embodiments the determination of the damage to the tissue comprises defining a damage-onset when a rate of the disappearance of the bubbles along the non-random pattern is below a predetermined threshold.

According to still further features in the described preferred embodiments the at least one parameter comprises at least one at least one ultrasound parameter.

According to still further features in the described preferred embodiments the at least one ultrasound parameter comprises echogenicity variations.

According to still further features in the described preferred embodiments the echogenicity variations comprise temporal echogenicity variations.

According to still further features in the described preferred embodiments the echogenicity variations comprise spatial echogenicity variations.

According to still further features in the described preferred embodiments the echogenicity variations comprise temporal echogenicity variations and spatial echogenicity variations.

According to still further features in the described preferred embodiments the determination of the damage to the tissue comprises defining at least one damage criterion based on the echogenicity variations, and defining a damage-onset when the at least one damage criterion is met.

According to still further features in the described preferred embodiments the at least one damage criterion comprises a substantial rise of an echogenicity of the tissue over a predetermined time-period while the heating is at a substantial constant rate.

According to still further features in the described preferred embodiments the at least one damage criterion comprises a moderate or no decrease of an echogenicity of the tissue over a predetermined time-period while the heating is at least temporarily ceased.

According to still further features in the described preferred embodiments the at least one damage criterion comprises at least an exponential rise of an echogenicity of the tissue while the heating is at a substantial constant rate.

According to still further features in the described preferred embodiments the at least one damage criterion comprises a random echogenicity gradient over a region of the ultrasound image while the heating is at least temporarily ceased.

According to yet another aspect of the present invention there is provided an apparatus for analyzing images of a tissue during a heat ablation procedure. The apparatus comprises: an input unit for receiving the images; an extractor for extracting from the images at least one parameter being indicative of a biological response to heat; and electronic-calculation functionality for determining damage to the tissue; using the parameter(s).

According to further features in preferred embodiments of the invention described below, the input unit is operable to receive the images substantially in real time.

According to still further features in the described preferred embodiments the apparatus further comprises an additional input unit for receiving heating information.

According to still another aspect of the present invention there is provided a system for destructing a target tissue. The system comprises: a heating apparatus, for delivering energy at a predetermined rate to thereby heat the target tissue; an imaging apparatus for providing images of at least a neighboring tissue to the target tissue; and a data processor, communicating with the heating apparatus and the imaging apparatus, and being supplemented by an apparatus having: an extractor, for extracting at least one parameter being indicative of a biological response to heat, and electronic-calculation functionality, for determining a damage to the neighboring tissue, using the at least one parameter.

According to further features in preferred embodiments of the invention described below, the imaging apparatus is selected from the group consisting of an ultrasound imaging apparatus, a magnetic resonance imaging apparatus, an X-ray imaging apparatus and a gamma imaging apparatus.

According to further features in preferred embodiments of the invention described below, the heating apparatus comprises at least one probe device adapted to be inserted endoscopically.

According to still further features in the described preferred embodiments the ultrasound apparatus comprises a probe device adapted to be mounted on an endoscope.

According to still further features in the described preferred embodiments the heating apparatus is selected from the group consisting of a radiofrequency ablating apparatus, a laser ablating apparatus, a focused ultrasound ablating apparatus and a microwave ablating apparatus.

According to still further features in the described preferred embodiments the electronic-calculation functionality is capable of identifying a substantial rise of an echogenicity of the tissue over a predetermined time-period while the tissue is heated at a substantial constant rate.

According to still further features in the described preferred embodiments the electronic-calculation functionality is capable of identifying a moderate or no decrease of an echogenicity of the tissue over a predetermined time-period while the heating is at least temporarily ceased.

According to still further features in the described preferred embodiments the to electronic-calculation functionality is capable of determining a functional dependence of a rise of an echogenicity of the tissue while the tissue is heated at a substantial constant rate, and comparing the functional dependence to an exponent.

According to still further features in the described preferred embodiments the electronic-calculation functionality is capable of calculating an echogenicity gradient over the ultrasound images.

The present invention successfully addresses the shortcomings of the presently known configurations by providing an apparatus for analyzing ultrasound images, a method of determining damage to a tissue and a method and system for destructing a tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 6*a-b* are ultrasound images captured during a thermal ablation procedure, performed in a mouse using laser irradiation delivered via an optical fiber, according to a preferred embodiment of the present invention;

FIGS. 7*a-d* are ultrasound images of a living (FIGS. 7*a-b*) and dead (FIGS. 7*c-d*) mouse, captured while heating a tumor (FIGS. 7*a* and 7*c*) and two minutes after the heating has been ceased (FIGS. 7*b* and 7*d*), according to a preferred embodiment of the present invention;

DESCRIPTION OF THE PREFERRED EMBODIMENTS

Figure 1:
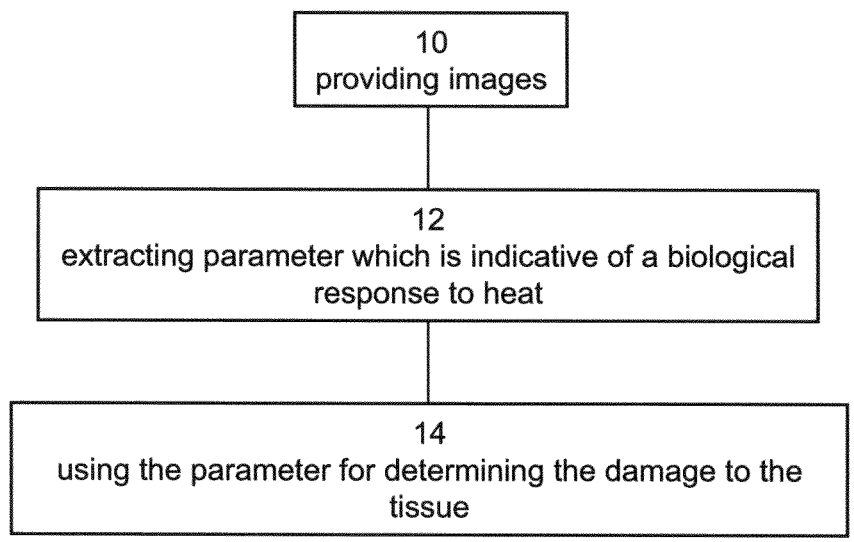
FIG. 1 is a flowchart diagram of method of determining damage to a tissue, according to a preferred embodiment of the present invention.

The present invention is of a method and system for ablating and monitoring tissue ablation, which can be used in many medical procedures, including, without limitation minimal invasive medical procedures. Specifically, the present invention can be used to determine level of damage to the treated tissue and/or a tissue neighboring the treated tissue. The present invention is further of an apparatus for analyzing images, which can be used for determining level of damage to tissues by image analysis.

The principles and operation of the methods, system and apparatus according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided a method of determining heat damage to a target tissue and/or a neighboring tissue during a heat ablation procedure. The method comprises the following method steps which are illustrated in the flowchart diagram of FIG. 1.

The target tissue is typically the tissue which is heat ablated during the heat ablation procedure, and can form any part of the human body, for example, an organ or a part of an organ, e.g., a tumor (malignant or benign) or any other pathological tissue, such as a restenotic tissue. The neighboring tissue is preferably in the periphery (immediate or farther) of the target tissue. Typically, but not obligatory, the neighboring tissue comprises tissue which is different from the target tissue. For example, if the target tissue is a tumor, the neighboring tissue preferably comprises normal cells being in proximity to the target tissue. Additionally, the neighboring tissue may comprise one or more blood vessels which provide blood circulation to the target tissue and the neighboring tissue.

Referring now to the drawings, in a first step of the method, designated by Block 10 in FIG. 1, images of the neighboring tissue and/or the target tissue are provided. Many types of images are contemplated. Representative examples include, without limitation, ultrasound images, magnetic resonance images, X-ray images, gamma images and the like.

According to a preferred embodiment of the present invention the images are a series of images or a series of batches of images captured at a rate which is selected so as to provide sufficient information to allow spatial as well as time-dependent analysis, as further detailed hereinbelow. The images are preferably captured substantially in real time so as to allow on-line monitoring of the heating process.

In a second step, designated by Block 12, one or more parameters are extracted from the images. The parameters are preferably indicative of a biological response of the neighboring tissue to heat. The biological response can be, for example, changes in blood circulation viability, heat convection or lack of heat convection via body liquid flow, accumulation of bubbles or lack thereof, disappearance pattern of bubbles and the like.

As demonstrated in the Examples section that follows, temporal and/or spatial variations of echogenicity is indicative of many biological responses, thus can serve, e.g., as a marker to the presence or absence of blood circulation in the neighboring tissue. Hence, according to a preferred embodiment of the present invention, the images are ultrasound images and the parameters are ultrasound parameters, such as, but not limited to, temporal and/or spatial variations of echogenicity.

It is expected that during the life of this patent many relevant diagnostic ultrasound methods defining new observables will be developed and the scope of the term ultrasound parameter is intended to include all such new methods a priori.

In a third step of the method, designated by Block 14, the parameter(s) are used for determining the damage to the neighboring tissue. This is preferably done by defusing a damage-onset when an appropriate damage criterion is met. In order to improve the accuracy of the damage assessment, several damage criteria can be employed, in any combination, as further detailed hereinunder and in the Examples section that follows.

Each damage criterion can be related either to the parameters or to the respective biological response. For example, in one embodiment the damage-onset is defined when changes in blood circulation viability are above a predetermined threshold, which can be expressed as a percentage (e.g., a decrement of about 50%, 60%, 70% or more in blood circulation viability). As demonstrated in the Example section that follows, most of the heat which is applied in the heating process is dispersed by blood circulation, which lowers the rate at which the temperature is increased. When the blood circulation is diminished, the cooling ability of the biological system is reduced and tissues in the neighboring tissue begin to experience higher temperatures, leading to their destruction.

As used herein the term "about" refers to ±10%.

In another embodiment, the damage-onset is defined when an accumulation of bubbles near the target tissue is above a predetermined threshold, while the heating is at a substantial constant rate. The accumulation of bubbles is preferably expressed as a rate at which the density of bubbles is increased, and the corresponding threshold can be defined as a percentage (e.g., an increment of about 5%, 10%, 15%, 20%, 25% or more in the density of bubbles).

According to the discovery of the present Inventors, the heating of a target tissue in presence of viable blood circulation may lead to a minor accumulation of bubbles. Moreover, even if a small amount of bubbles is formed during the heating process, this small amount disappears, immediately or shortly after the heating is ceased. This can be explained by the ability of blood flow to efficiently evacuate the bubbles away from the neighboring tissue. Conversely, if blood circulation (hence also heat convection) is absent or reduced a massive accumulation of bubbles takes place and remains for a prolonged time period even after the heating is ceased. Thus, a substantial rise in the rate of bubble formation over a relatively short period of time is indicative of a substantial rise in the heating rate, which results in elevated temperatures and tissue destruction.

At normal blood circulation, the evacuation of bubbles is typically along a pattern defined by the direction of blood flow which in turn is constrained by the orientation of the blood vessels. Hence, according to a preferred embodiment of the present invention the neighboring tissue is determined to be viable (i.e., not damaged) if the disappearance of the bubbles is along a non-random pattern, such as, along the orientation of the blood vessels. When the blood vessels are partially damaged, disappearance of bubbles occurs at a substantially lower rate but still along the same (non-random) pattern. When the damage to the blood vessels is aggravated, disappearance of bubbles (if occurs) is by random diffusion with substantially no spatial preference. Thus, according to a preferred embodiment of the present invention the damage-onset is defined when the rate of the disappearance of the bubbles along the non-random pattern is below a predetermined threshold or when a random disappearance of the bubbles is detected. The disappearance rate threshold can be expressed, for example, as unit density per unit time or any other suitable quantitative measure, such as area per unit time. Typically, the rate of disappearance when the blood vessels are damaged is reduced by a factor of five or ten, and the predetermined threshold is preferably selected accordingly. Representative examples of the predetermined threshold include, without limitation, any threshold from about 0.01 $cm^2$/min to about 0.1 $cm^2$/sec, more preferably from about 0.05 $cm^2$/min to about 0.5 $cm^2$/sec, most preferably from about 0.09 $cm^2$/min to about 0.9 $cm^2$/sec.

As stated, temporal and/or spatial echogenicity variations can be used as indicative for biological response of the tissue to heat. These echogenicity variations can be used for defining one or more damage criteria, with which, once met, a damage-onset can be identified. Many damage criteria are contemplated. For example, one damage criterion is preferably a substantial rise of the echogenicity of the target tissue over a predetermined time-period, while the heating is at a substantial constant rate. As further demonstrated in the Examples section that follows (see, e.g., FIGS. 8a-b), a damage-onset is characterized by a substantial abrupt rise in the echogenicity, because damage to blood vessels results in elevated temperatures and a substantial abrupt decrease in the ability of the biological system to evacuate gas.

It was found by the Inventors of the present invention that the rise in the echogenicity has a characteristic shape which can be fitted to an exponential function or any other function having a similar or steeper time-dependence. Thus, the time-dependence of the echogenicity can be used as a damage criterion whereby exponential or higher rise of the echogenicity, while heating the target tissue, corresponds to a damage-onset.

As stated, the bubbles which are accumulated when the blood circulation is absent or reduced, remain in the neighboring tissue for a prolonged period of time, even once the heating is ceased. This is because the residual mechanism for gas evacuation (e.g., random diffusion) is very inefficient. Thus, according to a preferred embodiment of the present invention the damage criterion can be a moderate or no decrease of the echogenicity of the target tissue over a predetermined time-period, while the heating is at least temporarily ceased.

An additional damage criterion can be related to the gradient (i.e., spatial derivative) of the echogenicity. As will be appreciated by one ordinarily skilled in the art, the gradient of the echogenicity at any given instant represents the spatial distribution of the bubbles, hence can be used to assess the aforementioned pattern along which the disappearance of bubbles occurs. As stated, when the blood circulation in the neighboring tissue does not function, the disappearance of bubbles (occurring when the heating is interrupted), has random spatial distribution because there is no directional mechanism (blood flow) controlling the evacuation of gas. Thus, according to a preferred embodiment of the present invention, the damage criterion is a random echogenicity gradient, while the heating is at least temporarily ceased.

According to another aspect of the present invention there is provided an apparatus 20 for analyzing images (e.g., ultrasound images, magnetic resonance images, X-ray images, gamma images) of a target tissue and a neighboring tissue during a heat ablation procedure.

Figure 2:
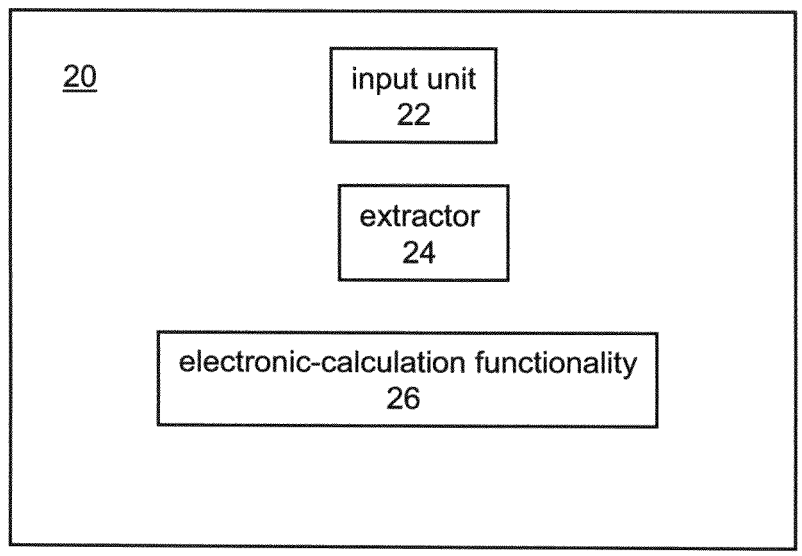
FIG. 2 is a schematic illustration of apparatus for analyzing images, according to a preferred embodiment of the present invention.

Reference is now made to FIG. 2, which is a schematic illustration of apparatus 20. Apparatus 20 comprises an input unit 22 for receiving the images. Input unit 22 preferably receives the images substantially in real time so as to allow to on-line monitoring; for example, in applications in which apparatus 20 is used in combination with ablating procedure. Apparatus 20 further comprises an extractor 24, for extracting parameters from the images, and electronic-calculation functionality 26 for determining the damage to the neighboring tissue, using at least one parameter. Electronic-calculation functionality 26 preferably executes a program of instructions compiled to allow applying one or more of the damage criteria. A suitable algorithm for employing a set of damage criteria is further detailed in the Examples section that follows (see Example 2 and FIG. 5).

Figure 3:
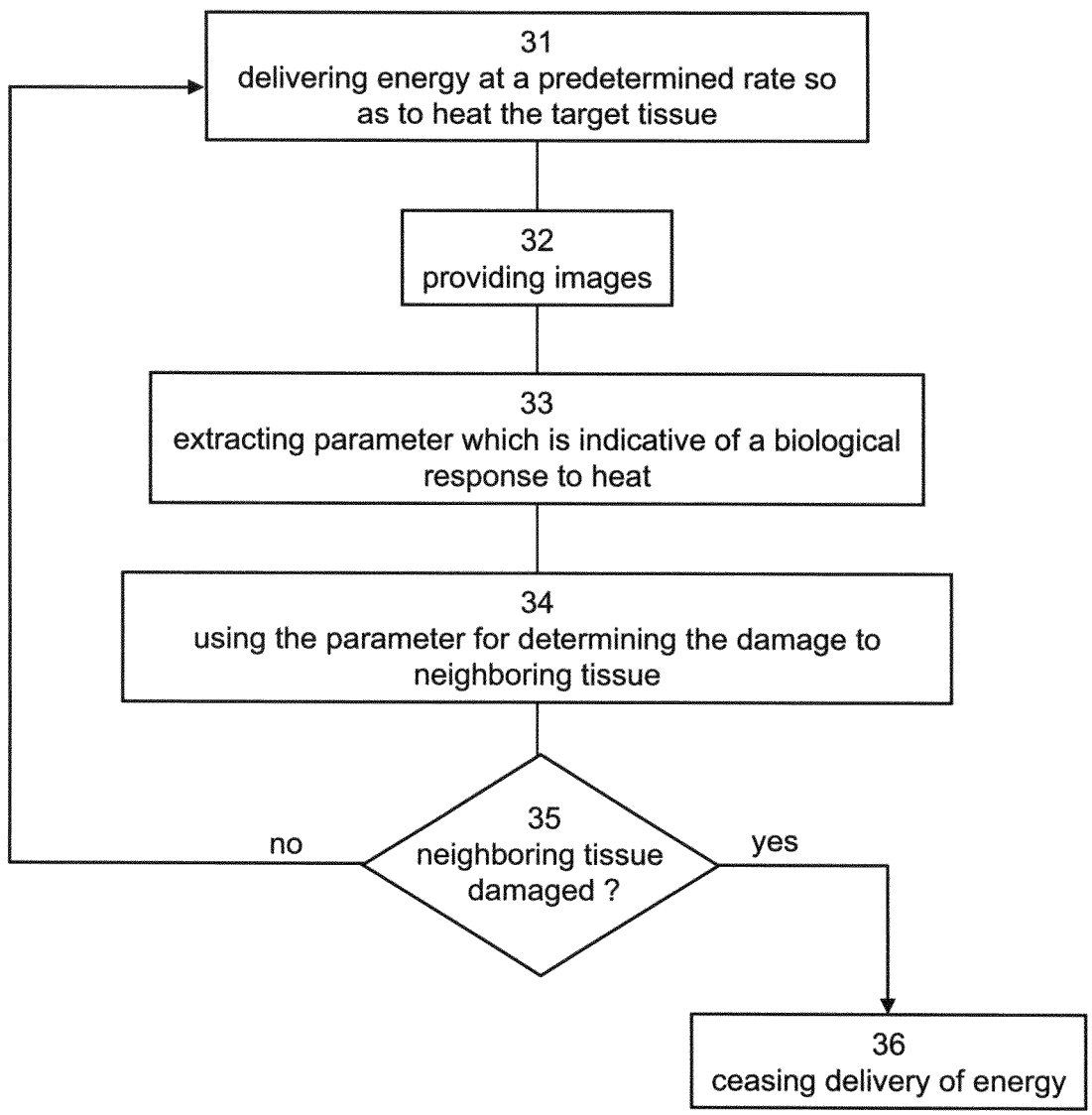
FIG. 3 is a flowchart diagram of method of a method of destructing a target tissue, according to a preferred embodiment of the present invention.

According to another aspect of the present invention there is provided a method of destructing a target tissue. The method comprises the following method steps which are illustrated in the flowchart diagram of FIG. 3.

In a first step of the method, designated by Block 31 energy is delivered at a predetermined rate so as to heat the target tissue. The energy can be delivered in many forms, including, without limitation, alternating electric field, laser light, focused ultrasound, microwave and the like. In a second step, designated by Block 32 images of the neighboring tissue and the target tissue are provided, and in a third step, designated by Block 33, one or more parameters which are indicative of the biological response of the neighboring tissue to heat are extracted from the images, as further detailed hereinabove. In a fifth step of the method, designated by Block 34, the parameter(s) are used for determining the damage to the neighboring tissue. In a fourth step of the method, designated by decision Block 35 and process Block 36, the delivery of energy is ceased, if neighboring tissue is damaged. If the neighboring tissue is not damaged, the method loops back to Block 31, and the delivery of energy is continued.

Figure 4:
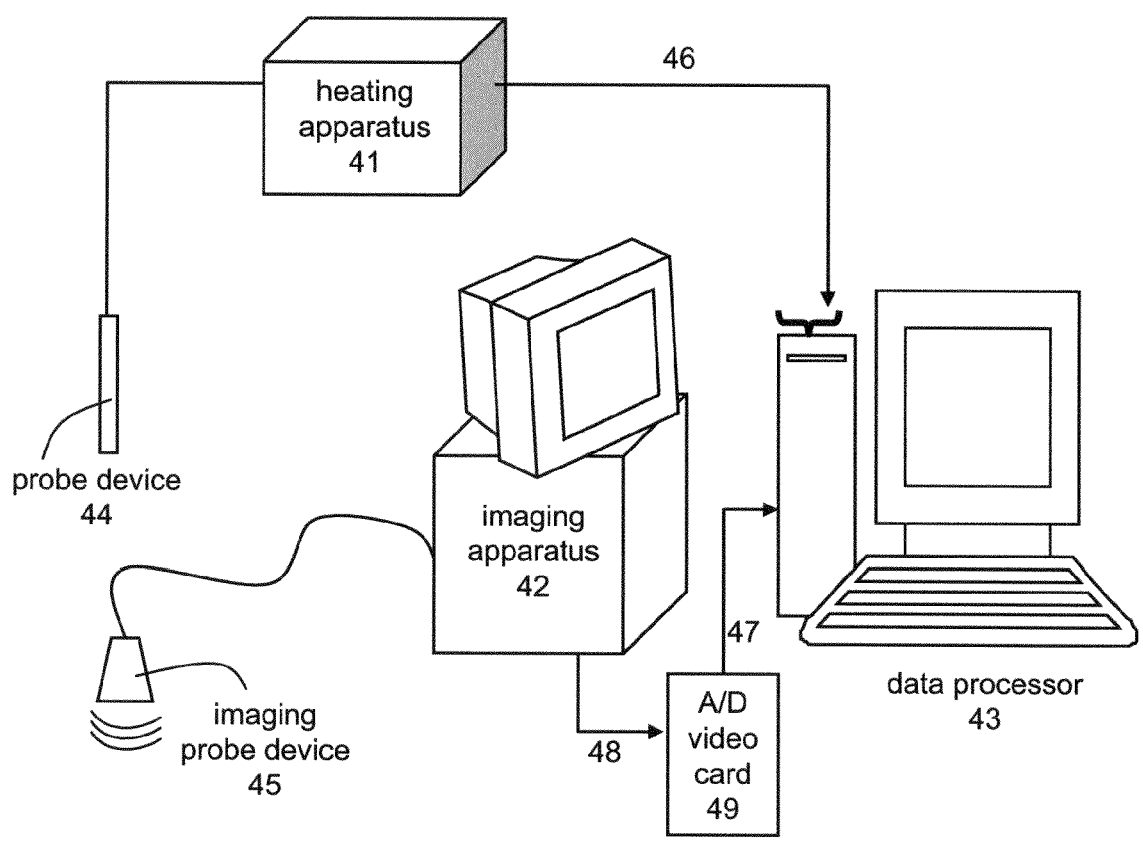
FIG. 4 is a schematic illustration of a system for destructing a target tissue, according to a preferred embodiment of the present invention.

Reference is now made to FIG. 4, which is a schematic illustration of a system 40 for destructing a target tissue, according to a preferred embodiment of the present invention. System 40 preferably comprises a heating apparatus 41, for delivering energy to the target tissue, an imaging apparatus 42 for providing an image of the target tissue and the neighboring tissue, and a data processor 43, communicating with heating apparatus 41 via communication line 46, and with imaging apparatus 42 via communication line 47. Imaging apparatus can be any imaging apparatus, including, without limitation an ultrasound imaging apparatus, a magnetic resonance imaging apparatus, an X-ray imaging apparatus and a gamma imaging apparatus.

Communication line 46 conveys heating information (e.g., onset, rate, power, synchronization, etc.) and can be connected, for example, to a parallel port of data processor 43. Communication line 47 conveys imagery information and can be connected, for example, to a universal serial bus (USB) port of data processor 43.

It is to be understood that other connection types between data processor 43 and apparati 41 and 42 are not excluded from the scope of the present invention.

Data processor 43 is preferably supplemented by apparatus 20 (not shown, see FIG. 2) for analyzing the images and determining the damage to neighboring tissue as further detailed hereinabove.

In the embodiment in which an ultrasound apparatus is employed, apparatus 42 preferably comprises an ultrasound probe device 45 which can be adapted to be mounted on an endoscope or to be used externally, as desired. Similarly, apparatus 41 preferably comprises one or more probe devices 44 adapted to be inserted endoscopically. In an alternative, yet preferred embodiment, heating apparatus 41 can be used externally. Many heating apparati are contemplated, including, without limitation a radiofrequency ablating apparatus, a laser ablating apparatus, a focused ultrasound ablating apparatus and a microwave ablating apparatus.

The communication between data processor 43 and imaging apparatus 42 is preferably through an analog-to-digital video card 49, which receives analog video signals from imaging apparatus 42 via communication 48, converts the analog signals into digital signals and transmits the digital signals to data processor 43 via communication line 47.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the to above descriptions illustrate the invention in a non limiting fashion.

Example 1

Blood Perfusion

In an experiment performed by the Inventors of the present invention, a 2 cm diameter tumor in a mouse was ablated for 15 minutes using a 10 watt laser operating in a pulsed mode of 1 second "on," 1 second "off." During the ablation, the emitted energy was 4500 joules. For a fifty percent transmission efficiency of the optical fiber, this amounts to 2250 joules delivered to the tissue. A large portion of the incident energy is dispersed by blood perfusion. There is a considerable level of uncertainty of the exact amount of energy which is dispersed by blood perfusion, due to several factors, such as the tumor stage, which can be in a varying degree of necrosis; and the level of blood vessel coagulation induced by the laser irradiation.

Relevant perfusion data range from 5 to 50 (measured in units of ml blood per 100 g tissue per minute), depending on tissue characteristics [Gunnar Brix et al., "Regional Blood Flow, Capillary Permeability, and Compartmental Volumes: Measurement with Dynamic CT—Initial Experience," Radiology, 210:269-276, 1999; Hori K et al., "Circadian Variation of Tumor Blood Flow in Rat Subcutaneous Tumors and its Alteration by Angiotensin II-Induced Hypertension," Cancer Res., 52(4):912-916, 1992; See [Welch A. J. and van Gemert M. J. C., "Optical Thermal response of Laser-Irradiated Tissue," Plenum, New York, 1995, chapter 14, Valdano J. W.].

It is appreciated that although the exact amount of blood perfusion can vary over a considerable scale, the ablative energy represents but a small fraction of the incident energy since the major part is taken away by blood perfusion.

Example 2

Analysis of Ultrasound Images

Following is a description of an algorithm, suitable for analyzing ultrasound images. The algorithm can be tangibly embodied by a machine-readable memory having a program of instructions executable by the machine for executing the algorithm.

It is to be understood that the algorithm presented in the present example, including the number, order and nature of the assignments and criteria which are employed thereby, are not to be considered as limiting.

The algorithm is preferably executed by a data processor having an input unit for receiving image information. The image information is preferably a plurality of digital signals, representing gray levels or colors of picture elements (e.g., pixels) of the ultrasound image. In principle, the steps of the algorithm are preferably applied on several picture elements, more preferable on all picture elements of the neighboring tissue, most preferably on all the picture elements of the ultrasound image. For simplicity, however, the following steps are for a single picture element, where a loop-wise repetition of the steps is to be taken over all picture elements participating in the analysis.

Figure 5:
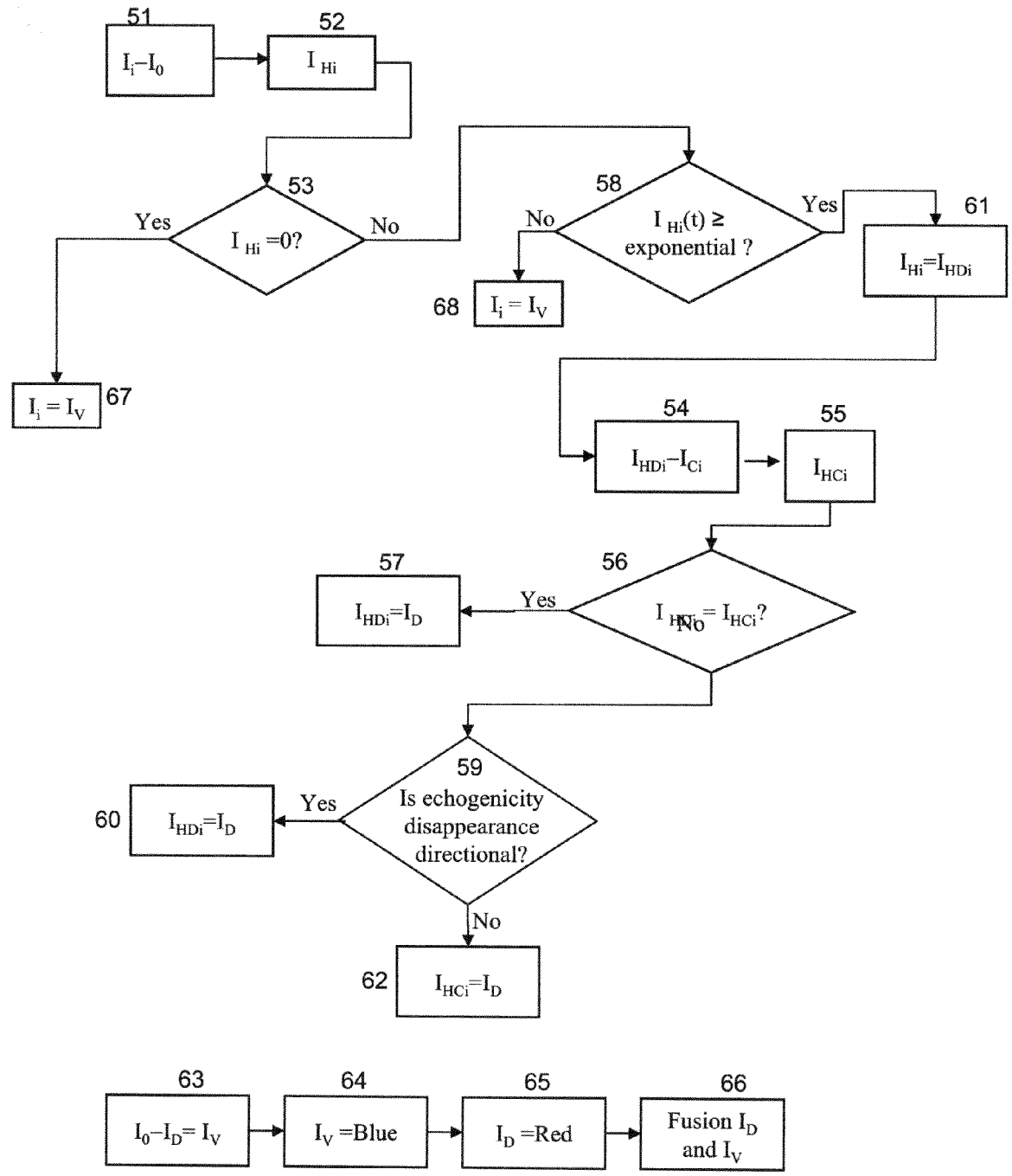
FIG. 5 is a flowchart diagram of an algorithm for analyzing images, according to a preferred embodiment of the present invention; the following variables are defined in the flowchart diagram: $I_0$ is the initial gray level, $I_i$ is the gray level during heating, $I_{Hi}$ is the gray level difference due to heating, $I_{Ci}$ is the gray level during cooling, $I_{HCi}$ is the gray level difference due to cooling, $I_D$ is the gray level of a damaged tissue and $I_V$ is the gray level of a viable tissue.

Reference is now made to FIG. 5 which is a flowchart diagram of the algorithm, according to a preferred embodiment of the present invention. Broadly speaking the algorithm stores a gray level value, $I_D$, whenever damage criteria are met, and a gray level, $I_V$, whenever the damage criteria are not met, in accordance with preferred embodiments of the present invention. Hence, the variables $I_D$ and $I_V$ below represent damaged and viable tissues, respectively.

Hence, the algorithm begins at Block 51, in which $I_0$, the initial gray level of the picture element (prior to the heating), is subtracted from $I_i$, the gray level of the picture element during heating. The algorithm progresses to Block 52 in which the subtraction result is assigned into a variable $I_{Hi}$, representing gray level difference due to heating. The algorithm proceeds to decision Block 53 and determines whether or not the value of $I_{Hi}$ equals zero. If $I_{Hi}=0$ the algorithm proceeds to Block 67 in which the pixel is marked as viable and the variable, $I_V$, representing a viable tissue is stored If $I_{Hi} \neq 0$, the algorithm proceeds to decision Block 58 and determines whether the functional dependence of $I_{Hi}$ on time (frame) is exponential or higher. For lower than exponential functional dependence of $I_{Hi}$, the algorithm proceeds to Block 68 in which $I_V$ is assigned to $I_i$. For exponential or higher functional dependence of $I_{Hi}$, the algorithm proceeds to Block 61. $I_{HDi}$ is assigned to $I_{Hi}$ representing the gray level difference caused by heating due to damage to blood vessels in the region. The algorithm proceeds to Block 54 in which the gray level of the picture element during cooling, $I_{Ci}$, is subtracted from $I_{HDi}$ and stored in a variable $I_{HCi}$ (Block 55). From Block 55 the algorithm proceeds to decision Block 56 and determines whether or not $I_{HDi}$ equals $I_{HCi}$. If $I_{HDi} = I_{HCi}$ the algorithm proceeds to Block 57 in which $I_D$ is assigned to $I_{HDi}$, otherwise ($I_{HDi} \neq I_{HCi}$), the algorithm proceeds to decision Block 59 and determines whether or not the disappearance of echogenicity is directional. For directional disappearance, the algorithm proceeds to Block 60 in which $I_D$ is assigned to $I_{HDi}$, and for non directional disappearance the algorithm proceeds to Block 62 in which $I_D$ is assigned to $I_{HCi}$.

Blocks 63-66 represent subtraction of $I_D$ from $I_0$ and assignment of the subtraction result into the variable $I_V$ (Block 63), assignment of a blue color to $I_V$ (Block 64), assignment of a red color for $I_D$ (Block 65) and fusion of $I_V$ and $I_D$ (Block 66) into a pictorial representation, so as to provide a map (see FIG. 9a, below) in which blue picture elements represent viable tissue and red picture elements represent damaged tissue.

Example 3

Ablating a Colon Cell Carcinoma by Laser

Materials and Methods

BALB/c mice were implanted subcutaneously with C26 colon cell carcinoma. Tumors were treated by a SHARPLAN 6020 diode laser system, emitting at 825 nm, using an interstitial fiber optic probe. During treatment, tissue effects were monitored and recorded by an ultrasound apparatus (Vivid3, General Electric) and the temperature was measured with thermocouples inserted in the tumor at different distances from the fiber optic probe end.

Twenty-four hours after treatment the mice were injected intraperitoneally with 1% Evans blue dye, and 24 hours later the mice were sacrificed, tumors were excised and 2-3 mm thick cross-section slices were cut. A section from the central area of each tumor was photographed with a color digital camera (model Camedia C-2000Z, Olympus) and compared with the ultrasound images obtained during monitoring. The injection of the dye into the blood system selectively stained viable tissue, leaving the necrotic tissue undyed.

Results

Increase in echogenicity in ultrasound tumor images was observed for light doses of 200-1800 Joules, although ultrasound tumor images did not correlate with temperature measurements. Changes in ultrasound images did not follow the changes in temperature caused by laser irradiation.

Following is an analysis of the physiological meaning of the echogenicity changes in ultrasound images during the ablation process.

FIGS. 6a-b are ultrasound images captured during a thermal ablation procedure, performed in a mouse using laser irradiation delivered via an optical fiber. FIG. 6a shows bubbles which were formed during the ablation and traveled through a viable blood vessel, in a neighboring tissue of tissue, emphasized in FIGS. 6a-b by an ellipse and designated by numeral 130. As shown in FIG. 6a, neighboring tissue 130 is relatively clear. FIG. 6b is an ultrasound image captured about 7 minutes after the image of FIG. 6a. As shown in FIG. 6b, the blood vessel was damaged and neighboring tissue 130 is turbid and filled with bubbles.

FIGS. 7a-d are ultrasound images of a living (FIGS. 7a-b) and dead (FIGS. 7c-d) mouse, captured while heating the tumor with a 10 watt laser light (FIG. 7a and FIG. 7c) and two minutes after the heating has been ceased (FIG. 7b and FIG. 7d). The tumor is marked on each of FIGS. 7a-d by an ellipse. As shown in FIG. 7a-b, in the presence of blood circulation of the living mouse, the heating process leads to a moderate and localized increment in the echogenicity which rapidly disappeared once the heating was ceased. On the other hand, in the absence of blood circulation (FIGS. 7c-d), the same energy leads to a dramatic increase in echogenicity of the entire the tumor. Yet, only a moderate decrease in echogenicity was observed after the termination of the heating process.

Figure 8A:
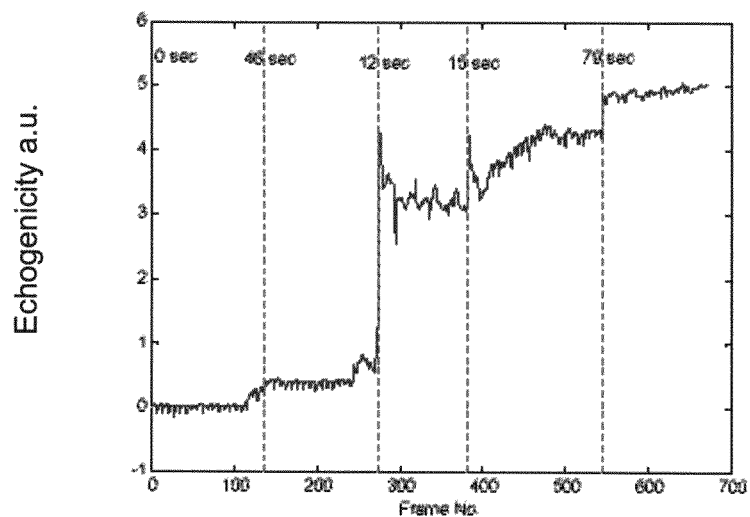
FIGS. 8*a-b* show quantitative data obtained from analysis of a series of ultrasound image batches captured during the ablation procedure, according to a preferred embodiment of the present invention.
Figure 8B:
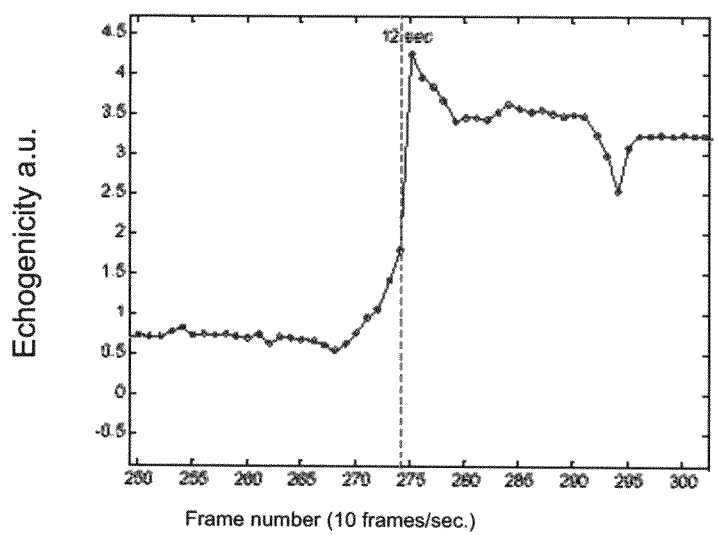

FIGS. 8a-b show quantitative data obtained from analysis of a series of ultrasound image batches captured during the ablation procedure. The analysis was performed by executing the steps of the algorithm as further detailed hereinabove (see Example 2 and FIG. 5). Shown in FIGS. 8a-b are plots of tissue damage in arbitrary echogenicity units as a function of the ablation time, where FIG. 8b is a magnification of the portion of FIG. 8a which corresponds to the time period between 250 and 300 seconds. Different time-windows (corresponding to different analyzed ultrasound image batches) are separated in FIGS. 8a-b by vertical dotted lines.

As shown in FIGS. 8a-b a substantially abrupt rise of the echogenicity was observed during the ablation process. According to a preferred embodiment of the present invention this rise is interpreted as an occurrence of damage to the neighboring tissue.

Figure 8C:
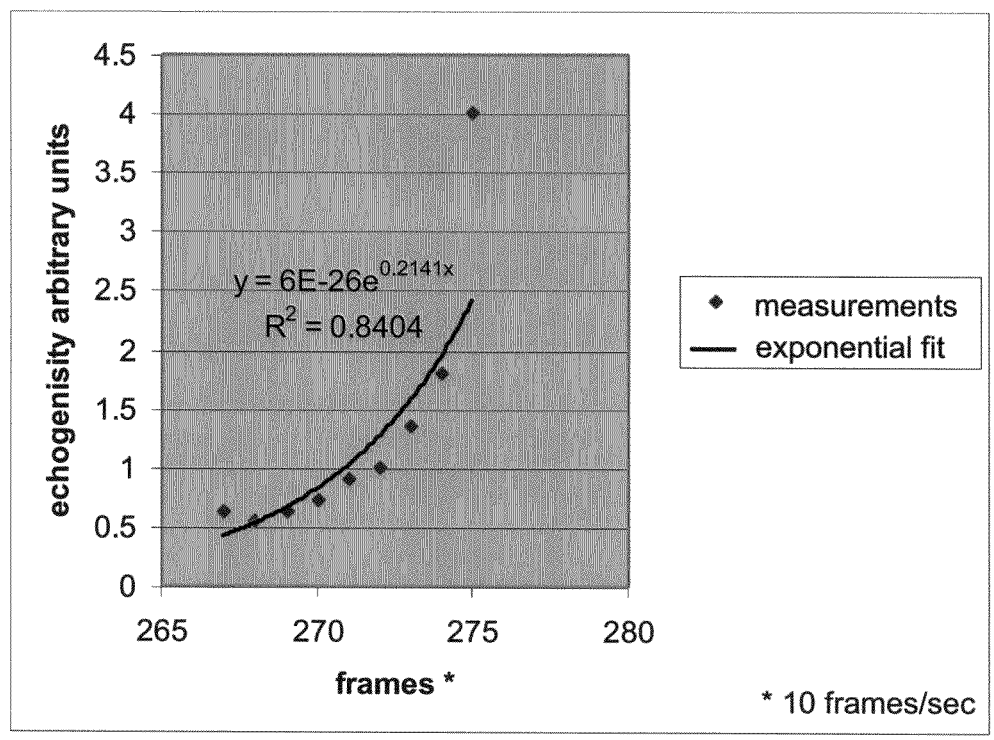
FIG. 8*c* shows a mathematical fit of the transition region of FIGS. 8*a-b*, according to a preferred embodiment of the present invention.

FIG. 8c shows a mathematical fit of the transition region of the echogenicity plots of FIGS. 8a-b. As shown, the time dependence of the echogenicity in the transition region is well described ($R^2 = 0.84$) by an exponential function $Ce^{\alpha x}$ where x represents time frames, $C = 6 \cdot 10^{-26}$ and $\alpha = 0.214$.

The golden standard for assessment of damage caused to tissue is pathology. Necrotic tissue can be assessed by vital staining, e.g., using Evans blue dye. A pathology assessment was performed on the dyed and undyed areas of the ablated region once removed from the mouse. The pathology assessment was compared to the analysis of ultrasound images performed according to a preferred embodiment of the present invention (see Example 2 and FIG. 5). The results are presented in FIGS. 9a-b and FIG. 10.

Figure 9A:
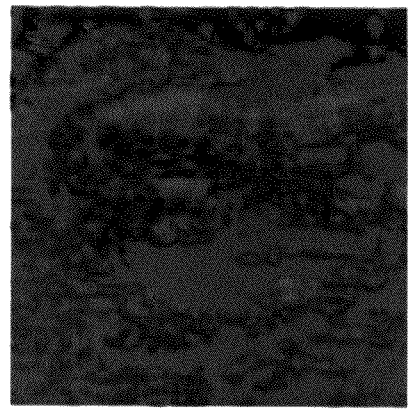
FIG. 9*a* shows analysis of ultrasound images according to a preferred embodiment of the present invention, where viable tissues are represented by blue areas and damaged tissues are represented by red areas.
Figure 9B:
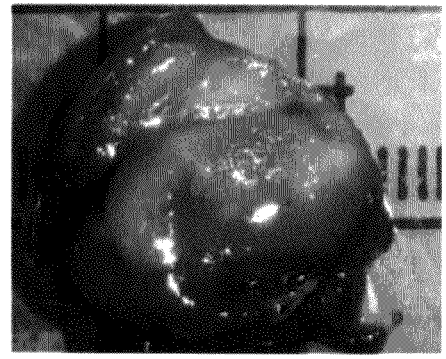
FIG. 9*b* is an image showing a pathology assessment of a tumor extracted from a mouse.

FIG. 9a shows the analysis of ultrasound images captured during the ablation process. Viable tissues are represented by blue areas (false colors) and damaged tissues are represented by red areas (false colors). FIG. 9b shows an image of tumor once extracted from the mouse. Viable tissues, dyed by Evans blue, are shown as blue areas in FIG. 9b and damaged (necrotic) tissues, which remained undyed, are shown as red areas. The correlations between the blue/red areas obtained by ultrasound image analysis in accordance with preferred embodiment of the present invention (FIG. 9a) and the blue/red areas in FIG. 9b, obtained by pathology assessment, are vivid.

Figure 10:
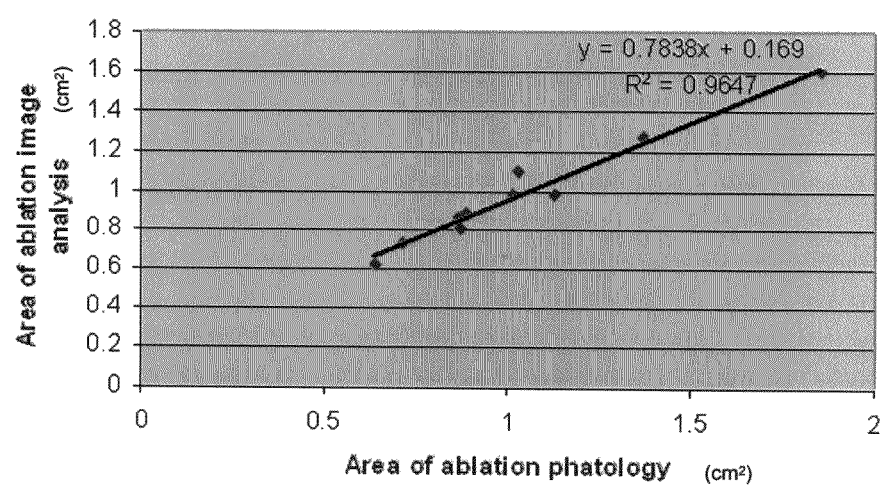
FIG. 10 is a quantitative correlation, for a number of cases, of the comparison of image analysis (e.g., FIG. 9*a*) and pathology assessment (e.g., FIG. 9*b*).

FIG. 10 is a quantitative correlation of the analysis of ultrasound images and the pathology assessment in various animals. Areas on the abscissa and the ordinate of FIG. 10 are in units of square centimeters. As shown in the Figure, a good correlation ($R^2 \approx 0.96$), was found between the necrotic area exhibited by pathological assessment, and the region of damaged tissue obtained via analysis of ultrasound images.

Discussion

Prior art attempts [Charles H. Cha et al., "CT Versus Sonography for Monitoring Radiofrequency Ablation in a Porcine Liver", Am. J. Roentgenology, 175:705-711, 2000] to monitor thermal ablation by examining bubble formation were unsuccessful because the output of the ablation procedure does not correlate with the formation of bubbles. As demonstrated in FIGS. 6a-8b, bubbles appear even when the tissue is still viable. When the heating process is interrupted or ceased, the blood to flow rapidly disperses the bubbles away from the target tissue.

The presence of bubbles per se does not indicate damage of tissue, because elevated temperatures in a medium (e.g., intra-cellular medium, extra-cellular medium, intra-vascular medium) are known to decrease the solubility of gases, hence to generate the conditions for gas efflux and bubble formation. Due to the expansion capability of the gas, it diffuses relatively rapidly through tissue. Moreover, determining damage to tissue solely by detection of bubbles can lead to a severe underestimation of the ablated region because bubbles can disappear rather rapidly [Phillips D, et al., "Acoustic backscatter properties of the particle/bubble ultrasound contrast agent," Ultrasonics 36:883-892, 1998; T. G. Leighton, "The Acoustic Bubble," Academic Press, London (1994), pp. 67-72 and 83-93; J. J. Bikerman, "Physical Surfaces," Academic Press, New York (1970), pp. 57-61]. Being a chaotic process, any combination of stable, unstable, large and small bubbles may be formed during the heating. Unstable bubbles may disappear very quickly, without any connection to the physiological state of tissue (or blood vessels in the region). Those regions can be interpreted as viable regardless if it is true or not. It is appreciated that such interpretation may result in underestimation of the damaged region, if the estimation is based on the absolute number or density of the detected bubbles.

On the other hand, a substantial rise in the rate of bubble formation over a relatively short period of time is indicative of damage to tissue because such a rise indicates that the heating rate (dT/dt) and/or gas evacuation rate has been changed. This can be explained by a change in the ability of body fluids to efficiently evacuate the gases which are released due to the elevated temperature, and because of loss in cooling capacity as a direct consequence of damage to blood vessels.

It was demonstrated in the present example that damage to blood vessels is manifested, inter alia, as a substantial abrupt increase in echogenicity. When the blood vessels in the neighboring tissue are damaged, the ultrasound image becomes opaque and the density of bubbles significantly increases (see FIGS. 6a-b). More abundant production of bubbles and a more stable state of high echogenicity was observed in absence of blood circulation, in accordance with preferred embodiments of the present invention. As stated, this phenomenon can be explained by the inability to evacuate the gases away from the neighboring tissue.

Quantitative analysis of the experimental data has demonstrated that the damage criterion can be defined based on the functional dependence of the echogenicity, whereby an exponential or higher rise (see FIG. 8c) in echogenicity indicates a damage-onset. Analysis of the ultrasound images in accordance with preferred embodiments of the present invention enabled the production of viability maps of the tissue under thermal ablation. The produced maps showed good correlation with pathological findings up to a millimeter scale resolution (see FIGS. 9a-b), hence demonstrating that assessment of damage to blood vessels can serve as a reliable tool to determine damage to other tissues in the neighboring tissue. The analysis of the ultrasound images presented herein is simple and reliable.

It is recognized that one of the main obstacles in tumor ablation is blood perfusion [Welch A. J. and van Gemert M. J. C., "Optical Thermal response of Laser-Irradiated Tissue," Plenum, New York, 1995]. Blood circulation has a significant role in the cooling capacity of a biological system. Detection of damage to blood vessels through a measurement of biological response to heat can therefore be used to reassure selective tumor destruction.

The experimental results presented herein demonstrate the ability of preferred embodiments of the present invention to provide on line detection of thermal ablation by diagnostic ultrasound. Unlike conventional techniques in which temperature measurements are employed, the present embodiments utilize physiology information which correlates with the viability status of the tissues in the neighboring tissue. The experimental data are in agreement with pathological findings as well as with numerical predictions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of monitoring heat damage to a volume of tissue during a heat ablation procedure, the method comprising:

employing an imaging device to obtain real-time images of a volume of tissue in an area undergoing said heat ablation procedure at an imaging rate;

employing a processor to carry out the steps of:

for each pixel in each of said real time images, extracting at least one parameter indicative of a biological response to heat in a portion of said tissue imaged in said pixel, said biological response comprising a decrement in blood circulation viability; and for each said pixel in each of said real time images, using an electronic calculation functionality, algorithmically determining based on said at least one parameter whether damage-onset has occurred in said portion of said tissue imaged in said pixel following exposure to heat in said heat ablation procedure; and displaying a differentiation image corresponding to each of said real-time images, such that in said differentiation image, pixels corresponding to tissue damaged by said heat ablation procedure appear different from pixels corresponding to viable tissue.

2. The method of claim 1, wherein said images are selected from a group consisting of non-Doppler ultrasound images, magnetic resonance images, X-ray images and gamma images.

3. The method of claim 1, wherein said determining whether damage-onset has occurred comprises defining damage-onset to be when said decrement in said blood circulation viability is above a predetermined threshold.

4. The method of claim 1, wherein said biological response comprises accumulation of bubbles near the tissue, while the heat ablation is at a substantially constant rate.

5. The method of claim 4, wherein said determining whether damage-onset has occurred comprises defining damage-onset to be when an increment in the density of said bubbles near the tissue is above a predetermined threshold.

6. The method of claim 1, wherein said biological response comprises disappearance of bubbles along a non-random pattern, while the heat ablation is at a substantially constant rate.

7. The method of claim 6, further comprising determining that said portion of said tissue imaged in said pixel is viable if said disappearance of said bubbles along said non-random pattern occurs.

8. The method of claim 6, wherein said determining whether damage-onset has occurred comprises defining damage-onset to be when a rate of said disappearance of said bubbles along said non-random pattern is below a predetermined threshold.

9. The method of claim 2, wherein said at least one parameter is a non-Doppler ultrasound parameter comprising echogenicity variations and said determining whether damage-onset has occurred comprises defining at least one damage criterion based on said echogenicity variations, and defining damage-onset to be when said at least one damage criterion is met.

10. The method of claim 9, wherein said at least one damage criterion comprises a substantial abrupt rise in echogenicity of said portion of said tissue over a predetermined time-period.

11. The method of claim 9, wherein said at least one damage criterion comprises a moderate decrease in echogenicity of said portion of said tissue over a predetermined time-period while the heat ablation is at least temporarily ceased.

12. The method of claim 9, wherein said at least one damage criterion comprises a rise in echogenicity of said portion of said tissue while the heat ablation is at a substantial constant rate, which rise can be fitted to an exponential function.

13. The method of claim 9, wherein said real time images comprise non-Doppler ultrasound images and wherein said at least one damage criterion comprises a random echogenicity gradient, corresponding to random spatial distribution of bubble disappearance, over a region of a non-Doppler ultrasound image while the heating is at least temporarily ceased.

14. A method of destructing a target tissue, the method comprising:
 delivering energy at a predetermined rate so as to heat the target tissue;
 executing the method of claim 1 to determine whether tissue neighboring said target tissue has been damaged; and
 if said neighboring tissue has been damaged, ceasing said delivery of said energy.

15. The method of claim 6, wherein said determining whether damage-onset has occurred comprises defining damage-onset to be said disappearance of said bubbles is in a random pattern.

16. A method of monitoring heat damage to a volume of tissue during a heat ablation procedure, the method comprising:
 employing an imaging device to obtain real-time images of a volume of tissue in an area undergoing said heat ablation procedure at an imaging rate;
 employing a processor to carry out the steps of:
  for each pixel in each of said real time images, extracting at least one parameter indicative of a biological response to heat in a portion of said tissue imaged in said pixel, said biological response comprising accumulation of bubbles near said tissue, while the heat ablation is at a substantially constant rate; and
  for each said pixel in each of said real time images, using an electronic calculation functionality, algorithmically determining based on said at least one parameter whether damage-onset has occurred in said portion of said tissue imaged in said pixel following exposure to heat in said heat ablation procedure; and
 displaying a differentiation image corresponding to each of said real-time images, such that in said differentiation image, pixels corresponding to tissue damaged by said heat ablation procedure appear different from pixels corresponding to viable tissue.

17. The method of claim 16, wherein said images are selected from a group consisting of non-Doppler ultrasound images, magnetic resonance images, X-ray images and gamma images.

18. The method of claim 16, wherein said determining whether damage-onset has occurred comprises defining damage-onset to be when an increment in the density of said bubbles near the tissue is above a predetermined threshold.

19. The method of claim 16, wherein said biological response comprises disappearance of bubbles along a non-random pattern, while the heat ablation is at a substantially constant rate.

20. The method of claim 19, further comprising determining that said portion of said tissue imaged in said pixel is viable if said disappearance of said bubbles along said non-random pattern occurs.

21. The method of claim 19, wherein said determining whether damage-onset has occurred comprises defining damage-onset to be when a rate of said disappearance of said bubbles along said non-random pattern is below a predetermined threshold.

22. The method of claim 17, wherein said at least one parameter is a non-Doppler ultrasound parameter comprising echogenicity variations and said determining whether damage-onset has occurred comprises defining at least one damage criterion based on said echogenicity variations, and defining damage-onset to be when said at least one damage criterion is met.

23. The method of claim 22, wherein said at least one damage criterion comprises a substantial abrupt rise in echogenicity of said portion of said tissue over a predetermined time-period.

24. The method of claim 22, wherein said at least one damage criterion comprises a moderate decrease in echogenicity of said portion of said tissue over a predetermined time-period while the heat ablation is at least temporarily ceased.

25. The method of claim 22, wherein said at least one damage criterion comprises a rise in echogenicity of said portion of said tissue while the heat ablation is at a substantial constant rate, which rise can be fitted to an exponential function.

26. The method of claim 22, wherein said real time images comprise non-Doppler ultrasound images and wherein said at least one damage criterion comprises a random echogenicity gradient, corresponding to random spatial distribution of bubble disappearance, over a region of a non-Doppler ultrasound image while the heating is at least temporarily ceased.

27. A method of destructing a target tissue, the method comprising:
delivering energy at a predetermined rate so as to heat the target tissue;
executing the method of claim 16 to determine whether tissue neighboring said target tissue has been damaged; and
if said neighboring tissue has been damaged, ceasing said delivery of said energy.

28. The method of claim 19, wherein said determining whether damage-onset has occurred comprises defining damage-onset to be said disappearance of said bubbles is in a random pattern.

29. A method of monitoring heat damage to a volume of tissue during a heat ablation procedure, the method comprising:
employing an imaging device to obtain real-time images of a volume of tissue in an area undergoing said heat ablation procedure at an imaging rate;
employing a processor to carry out the steps of:
for each pixel in each of said real time images, extracting at least one parameter indicative of a biological response to heat in a portion of said tissue imaged in said pixel, said biological response comprising disappearance of bubbles along a non-random pattern, while the heat ablation is at a substantially constant rate; and
for each said pixel in each of said real time images, using an electronic calculation functionality, algorithmically determining based on said at least one parameter whether damage-onset has occurred in said portion of said tissue imaged in said pixel following exposure to heat in said heat ablation procedure; and
displaying a differentiation image corresponding to each of said real-time images, such that in said differentiation image, pixels corresponding to tissue damaged by said heat ablation procedure appear different from pixels corresponding to viable tissue.

30. The method of claim 29, wherein said images are selected from a group consisting of non-Doppler ultrasound images, magnetic resonance images, X-ray images and gamma images.

31. The method of claim 29, further comprising determining that said portion of said tissue imaged in said pixel is viable if said disappearance of said bubbles along said non-random pattern occurs.

32. The method of claim 29, wherein said determining whether damage-onset has occurred comprises defining damage-onset to be when a rate of said disappearance of said bubbles along said non-random pattern is below a predetermined threshold.

33. The method of claim 30, wherein said at least one parameter is a non-Doppler ultrasound parameter comprising echogenicity variations and said determining whether damage-onset has occurred comprises defining at least one damage criterion based on said echogenicity variations, and defining damage-onset to be when said at least one damage criterion is met.

34. The method of claim 33, wherein said at least one damage criterion comprises a substantial abrupt rise in echogenicity of said portion of said tissue over a predetermined time-period.

35. The method of claim 33, wherein said at least one damage criterion comprises a moderate decrease in echogenicity of said portion of said tissue over a predetermined time-period while the heat ablation is at least temporarily ceased.

36. The method of claim 33, wherein said at least one damage criterion comprises a rise in echogenicity of said portion of said tissue while the heat ablation is at a substantial constant rate, which rise can be fitted to an exponential function.

37. The method of claim 33, wherein said real time images comprise non-Doppler ultrasound images and wherein said at least one damage criterion comprises a random echogenicity gradient, corresponding to random spatial distribution of bubble disappearance, over a region of a non-Doppler ultrasound image while the heating is at least temporarily ceased.

38. A method of destructing a target tissue, the method comprising:
delivering energy at a predetermined rate so as to heat the target tissue;
executing the method of claim 29 to determine whether tissue neighboring said target tissue has been damaged; and
if said neighboring tissue has been damaged, ceasing said delivery of said energy.

39. The method of claim 29, wherein said determining whether damage-onset has occurred comprises defining damage-onset to be said disappearance of said bubbles is in a random pattern.

* * * * *